United States Patent [19]

Ray

[11] Patent Number: 4,944,744
[45] Date of Patent: Jul. 31, 1990

[54] BONE IMPACTORS

[75] Inventor: Charles D. Ray, Wayzata, Minn.

[73] Assignee: Surgical Dynamics, Inc., Alameda, Calif.

[21] Appl. No.: 887,607

[22] Filed: Jul. 17, 1986

Related U.S. Application Data

[63] Continuation-in-part of Ser. No. 731,024, May 6, 1985, Pat. No. 4,657,002.

[51] Int. Cl.⁵ ............................................. A61B 17/16
[52] U.S. Cl. .................................... 606/79; 606/84; 606/90; 606/105
[58] Field of Search ........... 128/92 V, 303 R, 92 VT; 606/79–85, 90, 105

[56] References Cited

U.S. PATENT DOCUMENTS

| D. 249,705 | 9/1978 | London | 128/92 VL |
| 4,657,002 | 4/1987 | Ray | 128/92 VT |

FOREIGN PATENT DOCUMENTS 721086  3/1980  U.S.S.R. .

OTHER PUBLICATIONS

"Lumbar Spondylophyte Impaction Set", a brochure from Karlin Technology, Venice, CA (no date).
*Spine*, vol. 11, No. 10, pp. 1051–1053, Dec. 1986, "Bone Impactors", by Charles D. Ray.

*Primary Examiner*—C. Fred Rosenbaum
*Attorney, Agent, or Firm*—Fliesler, Dubb, Meyer & Lovejoy

[57] ABSTRACT

A bone impactor consists of a single piece of lightweight metal which has a handle and a smooth shank, across the tip of which extends a working surface that may be fitted against an excrescence, followed by striking the butt end of the handle to compress the excrescence into the bone to relieve pressure on a nerve. The shank of the bone impactor terminates in a foot that tapers to a toe, and a flat working surface beneath the foot makes an angle of at least 95° with the longitudinal axis of the shank.

4 Claims, 2 Drawing Sheets

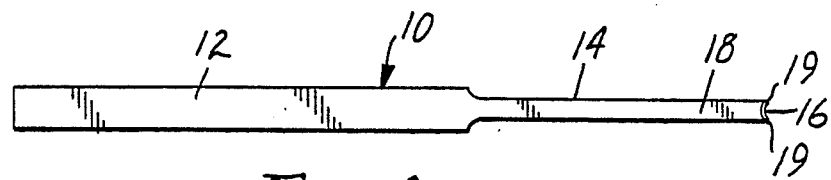
FIG. 1
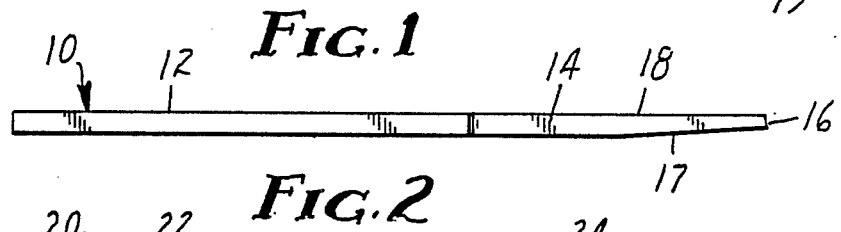
FIG. 2
FIG. 3
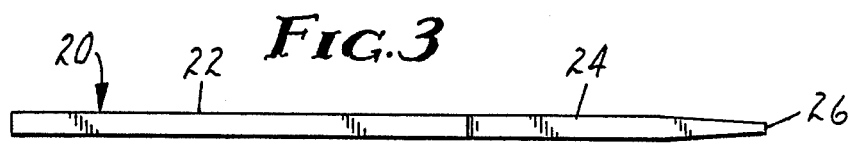
FIG. 4
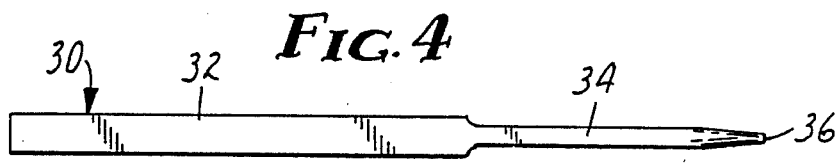
FIG. 5
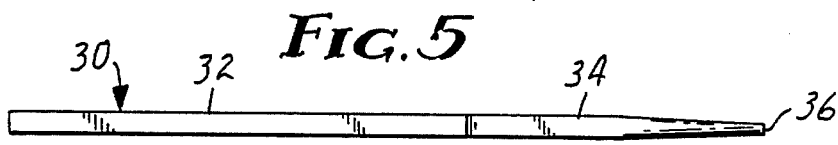
FIG. 6
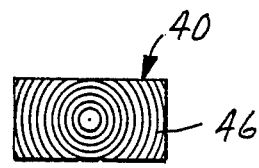
FIG. 7

BONE IMPACTORS

CROSS-REFERENCE TO RELATED APPLICATION

This application is a continuation-in-part of copending application Ser. No. 731,024, filed May 6, 1985, now U.S. Pat. No. 4,657,002.

BACKGROUND OF THE INVENTION

1. Field of the Invention

The invention concerns bone impactors which are useful for compressing bone excrescences to relieve pressure on a nerve and are especially useful for spinal decompresssion.

2. Description of Related Art

A major cause of spinal stenosis or entrapment of neutral tissues is the presence of hyperostoses, bone spurs, disc bars, osteophytes, and other excrescences from bony or bony/ligamentous overgrowth. The usual surgical procedure for relieving the consequent compression of the neutral tissues and attendant blood vessels is to cut off the excrescence with an osteotome or a high speed air drill. All bony structures have two principle layers: an outer hard layer called the cortex and a softer, spongy inner layer called the cancellous portion. If the cortical portion is cut away in order to eliminate an excrescence, this may weaken the bone, possibly promote an overgrowth of the cancellous portion and hence a return of the excrescence, or may leave an irregular surface against which the nerve must lie. Furthermore, bone is covered with membranes and often with ligaments which when cut away in the usual fashion (air drills and osteotomes) may leave behind ragged edges of the adherent soft tissues. This may promote fibrosis (scar tissue formation).

Among the most common locations for compression of nerve and blood vessels in the human spine is the area that lies adjacent to an oval structure known as the pedicle. Major nerves coming out of the spinal cord and its containing sac pass around and beneath the pedicle almost like a rope passing around a pulley. Overgrowth of a portion of the pedicle may produce nerve compression which may be relieved by cutting away the overgrowth, but the cutting of this overgrowth or of any other excrescence may be difficult and lead to complications. For example, upon cutting away a bone spur which is a mixture of calcific and soft tissue along the margins of a disc bar, the remaining surfaces may be quite irregular or torn, and this may lead to redevelopment of spurs or to epidural or perineural fibrosis. Furthermore, the neural tissue is usually in such close proximity to the spur that removing it present a mechanical hazard.

I am aware of only one publication which suggests the use of a bone impactor to compress bone to relieve pressure on nerve tissue, namely U.S.S.R. Author's Certificate No. 721086 (V.T. Pustovoitenko) published Mar. 15, 1980 in Bulletin No. 10 and having a date of publication of Mar. 25, 1980. As shown in the drawing, the bone impactor has a curved tip which is inserted between the anterior wall of the dural sac and the posterior wall of the vertebral body by passing around the sac laterally. A notch in the curved tip of the bone impactor is placed over a prominent bony process or excrescence of a fractured vertebra. By striking the butt end of the bone impactor, a portion of said process is compressed. While that procedure should decompress the nerve tissue more easily and with less hazard than would cutting away the process, a fracture of this type which produces a nerve compression is rare. Hence, there would be very little use for the U.S.S R. bone impactor.

Bone impactors are widely used for driving bone and for packing bone chips. A catalog of Richards, Inc. Memphis, TN shows a number of instruments which can be used as bone impactors, e.g., "Tibial Component Impactor", Catalog No. 11-0225, "Jewett Bone Chip Packers", Catalog No. 11-0991, etc., "T-Handled Elevator", Catalog No. 11-1148, and "Hob-nail Impactro", Catolog No. 11-1154, the working surface of which has a diamond knurl. A catalog of Codman Instrument Co. show a Cloward "Bone Graft Impactor, double ended", Catalog No. 28-1000. None of those instruments would be useful for decompressing nerve tissue.

BRIEF SUMMARY OF THE INVENTION

The invention concerns one of a set of five bone impactors by which a bone excrescence can be compressed instead of being cut away to relieve pressure on a nerve and associated blood vessels. Each of those bone impactors has a handle and a shank which preferably lie in a substantially straight line so that forces can be squarely transmitted to an excrescence by striking the butt end of the handle, thus minimizing any danger of slippage. In the first three of those bone impactors (shown in FIGS. 1-6 of the drawing), the shank is thinner than the handle, while a fourth (shown in FIG. 7) may have a handle and shank which are indistinguishable from each other, each having the same uniform, rectangular cross section. Those four bone impactors are disclosed and claimed in my above-cited U.S. Pat. No. 4,657,002.

The fifth bone impactor of the set, which is the subject of this invention, is similar in construction to the three bone impactors of FIGS. 1-6 except that its shank terminates in a foot that resembles a shoe on a human foot. The foot tapers to a toe which is blunt and yet sufficiently thin to minimize the lifting of a nerve or dura under which it may be inserted. Beneath the foot is a rectangular working surface which makes an obtuse angle of more than 95° with the direction of attack (i.e., the longitudinal axis of the shank) of the bone impactor in order fit better to the anatomy and also to facilitate entry beneath a nerve or dura. Preferably that angle is at least 105° but not so great as to create any danger of slippage, i.e., not more than about 125°.

Except for the third bone impactor of the set which has a circular working surface, the handle should be shaped to indicate the orientation of the working surface. A handle of uniform rectangular cross section is economical to manufacture and quite suitable for this purpose.

When the working surface of a bone impactor is small relative to the handle, the cross-sectional area of the shank should be substantially smaller than that of the handle, thus enhancing insertion of the shank into the incision and also minimizing visual interference.

Each edge of each workng surface of the bone impactors should have a radius of at least 0.1 mm to avoid cutting any excrescence to be impacted.

BRIEF DESCRIPTION OF THE DRAWING

The drawing illustrates the five above-described bone impactors of the invention, each of which is a single piece of lightweight metal such a anodized aluminum. In the drawing:

FIG. 1 is a top view of a first of my set of five bone impactors;

FIG. 2 is a side elevation of the bone impactor of FIG. 1;

FIG. 3 is a top view of a second of my set of bone impactors;

FIG. 4 is a side elevation of the bone impactor of FIG. 3;

FIG. 5 is a top view of a third of my set of bone impactors;

FIG. 6 is a side elevation of the bone impactor of FIG. 5;

FIG. 7 is an end view, enlarged in comparison to FIGS 1-6, showing the working surface of a fourth bone impactor which completes a set of four bone impactors sufficient to compress almost any excrescence.

Figure 8:
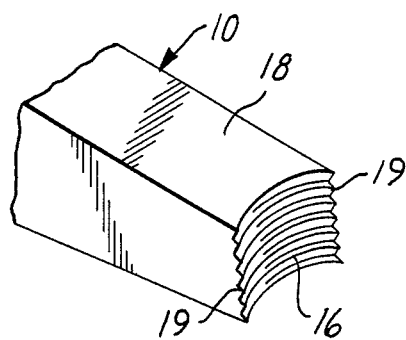
FIG. 8 is a prospective view of a preferred working surface for the bone impactor of FIGS. 1 and 2, greatly enlarged.

The bone impactor 10 shown in FIGS. 1 and 2 consists of a handle 12 and a shank 14 which lie in a straight line. Across the tip of the shank is a working surface 16 which forms a cylindrical concavity. The axis of that cylindrical surface extends at an angle of about 70° with said straight line, namely, the direction in which forces are trasmitted upon striking the butt end of the handle 12 while the concave working surface 16 is fitted against a bone excrescence. The face 17 of the shank 14 with which the concave working surface 16 makes an acute angle is tapered inwardly toward the concave working face, whereas the opposite face 18 of the shank 14 is straight over its full length for reasons explained above. In a prototype of the bone impactor 10, the handle 12 is about 15 cm in length, 1.1 cm in width, and 0.6 cm in thickness; the shank 14 is about 10 cm in length; the height of the cylinder formed in the working surface 16 is 0.3 cm; and the length of the chord between the circumferential extremities 19 of the cylinder is 0.6 cm.

The bone impactor 20 shown in FIGS. 3 and 4 has a handle 22 and a shank 24 which becomes smaller toward its flat, rectangular working surface 26. In a prototype of the impactor 20, the working surface 26 is 0.3 by 0.6 cm, with the long dimension extending in the same direction as the broad side of the handle 22.

The bone impactor 30 shown in FIGS. 5 and 6 has a handle 32 and a shank 34, across the tip of which is a small, circular working surface 36. In a prototype of the bone impactor 30, the diameter of the circular working surface 26 is 0.3 cm.

The handle and shank of the bone impactor 40 shown in FIG. 7 are of uniform cross section, and the flat working surface 46 at the tip of the shank is formed with knurls in concentric circles. In a prototype of the impactor 40, the working surface is 1.1 by 0.6 cm.

Preferably the working surface 16 of the bone impactor 10 of FIGS. 1 and 2 has a linear knurl as shown in FIG. 8, thus resulting in a sawtooth appearance when the impactor is viewed from the side.

Figure 9:
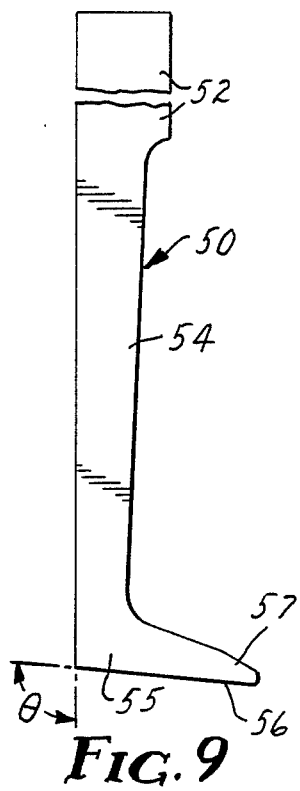
FIG. 9 is a side elevation of a fifth bone impactor of my set, i.e, the bone impactor of the invention.

The bone impactor 50 shown in FIG. 9 has a handle 52 and a shank 54 which lie in a straight line that conincides with the direction of attack. The shank terminates in a foot 55 which tapers to a toe 57. Beneath the foot is a flat working surface 56 which preferably has a diamond knurl (not shown). The edges of the working surface of each of the five prototype bone impactors have been buffed, thus producing a radius of about 0.2 mm at each edge to minimize cutting upon impacting an excrescence.

The spinal surgical procedures for which the bone impactors of the invention are most needed involved lateral stenosis, and the areas of entrapment of nerve roots and ganglia are medial or inferior to the region of the pedicle. These areas are rather difficult to reach, especially via approaches from the dorsal midline in the lumbar spine. Portions of the superior, lateral or inferior lamina must be removed in order to reach the nerve or ganglion and the assiocated, offending excrescence. Approaches from the far lateral direction may spare most of the posterior and lateral structures. The posterior unroofing of nerve, if needed, is usually accompanied by an anterior decompression such as the impaction of an osteophyte, ventral to the nerve.

The progression of approach to a lateral stenosis may involve the lamina and facet (dorsal to the nerve root), the vertebral body and spur (ventral to the nerve structures), and the pedicle (cephalad to the nerve structures). In this situation, following the more dorsal decompression from a rather lateral approach, the pedicle may be moved away from the ganglion by cutting through the cancellous portion with an osteotome and then impacting the hard cortical portion into the partially resected cancellous portion. In this way, the medial and inferior portions of the pedicle (around which the nerve and ganglion must "wrap") are displaced away from the nerve to decompress it.

Another excellent application for impaction is along the posterior ridge of a disc bar. After removal of a bulging herinated disc, one may find that a rigid ridge remains quite prominently beneath the traversing nerve root or dural sac. In most such cases, impaction is a superior means for displacing the offensing excrescence or disc bar from the nerve, leaving behind a relatively smooth surface. In a rather similar application, the disc bar and step-off of a spondylolisthesis may be impacted so that the nerve roots passing over the step will be relaxed and drawn over a much less actuely localized displacement against the ventral surface of the dural sac. Sometimes one may find the process of localized decompression easier to perform where the cortical surface is first fractured by one of the bone impactors and the remaining bone fragments lifted out.

Figure 10:
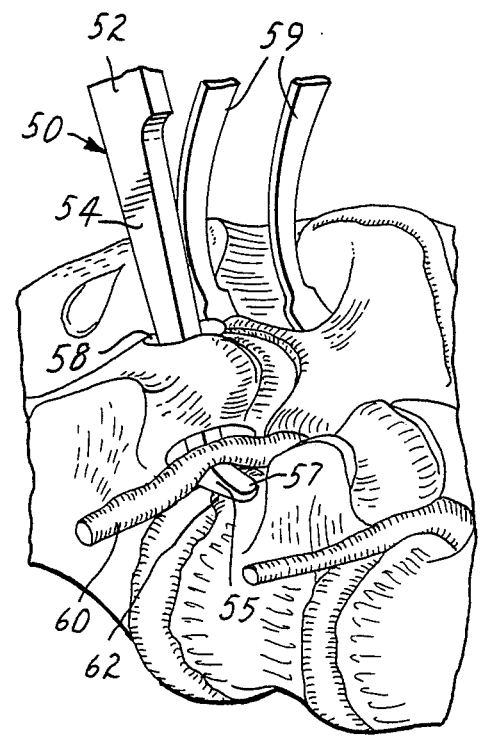
FIG. 10 is a perspective view of a portion of a human spinal column showing a use for the bone impactor of FIG. 9.

Referring to FIG. 10, the bone impactor 50 has been inserted through a hole 58 that has been drilled through the facet joint at the fifth lumbar level. While a jack 59 holds the facet joint open, the toe 57 of the impactor is inserted into the hole and slipped under the nerve 60 so that its foot 55 rests against a bone spur or osteophyte 62 that has formed on the vertebral body. Upon striking the butt end of the impactor 50, the foot is driven into the osteophyte, thus decompressing the nerve. After removing the bone impactor, a small fat graft can be placed at the base of the hole 58 followed by driving a bone dowel into the hole, and a subsequent posterolateral intertransverse process fusion is performed.

In a prototype of the bone impactor 50, the working surface 56 makes an angle of 105° with said straight line (i.e., the longitudinal axis of the shank) and is 10 mm long and 3 mm wide. The toe 57 is 1.0 mm thick at its extremity, and the foot 55 is 3.0 mm thick where it diverges from the shank. The prototype fits nicely through an 11-mm hole which can be repaired with a 12-mm bone dowel.

In the foregoing procedure after drilling the hole, a single tool (the bone impactor) is inserted deep into the wound, versus the use in the prior art of a first tool to move the nerve (an act fraught with danger) and a second tool to cut away or otherwise eliminate the osteophyte. In contrast, the design of the bone impactor 50 requires minimal movement of the nerve and virtually no danger to the nerve while impacting the excrescence. It also permits the hole to be quite small and hence easy to repair with a bone dowel. Prefereably the foot 55 is no longer than the above-described prototype, but can be smaller to permit the bored hole to be smaller. Although the foot should not be so small as to involve any risk of breakage, there should be minimal risk when the foot has a length of at least 5 mm and a width of at least 2 mm.

In addition to its utility in the above-described procedure, the bone impactor 50 can be inserted through the intralaminar space between adjacent vertebrae to impact osteophytes which can be reached without drilling a hole. The same impactor also can be used to impact osteophytes lateral to the facet joint which can be reached by turning the toe of the foot inward.

I claim:

1. A bone impactor which is useful for compressing a bone excrescence to relieve pressure on a nerve and comprises a handle and a shank which terminates in a foot that tapers to a thin toe, and a flat working surface beneath the foot that makes an angle of at least 95° with the longitudinal axis of the shank of the impactor, each edge of the working surface having a radius of at least 0.1 mm.

2. A bone impactor as defined in claim 1 wherein said angle angle is not more than about 125° and the flat working surface is formed with knurls.

3. A bone impactor as defined in claim 2 wherein the thickness of the toe at its extremity is about 1.0 mm, and the foot is about 3.0 mm thick where it diverges from the shank.

4. A bone impactor as defined in claim 1 wherein said angle is about 150°.

* * * * *